(12) United States Patent
Lee et al.

(10) Patent No.: US 9,107,951 B2
(45) Date of Patent: *Aug. 18, 2015

(54) CALCIUM PARTICLE-EMBEDDED, SNAP-TO-DOUGH, HIGH-VISCOSITY BONE CEMENT

(75) Inventors: Samuel Lee, San Francisco, CA (US); Joerg Meyer, Heusenstamm (DE); Robert Wenz, Wollstadt (DE); Thomas A Slater, Sunnyvale, CA (US); Ann M. Heike, Redwood City, CA (US)

(73) Assignee: KYPHON SARL, Neuchatel (CH)

( * ) Notice: Subject to any disclaimer, the term of this patent is extended or adjusted under 35 U.S.C. 154(b) by 33 days.

This patent is subject to a terminal disclaimer.

(21) Appl. No.: 13/812,364

(22) PCT Filed: Jul. 26, 2011

(86) PCT No.: PCT/US2011/045338
§ 371 (c)(1),
(2), (4) Date: Apr. 12, 2013

(87) PCT Pub. No.: WO2012/018612
PCT Pub. Date: Feb. 9, 2012

(65) Prior Publication Data
US 2013/0210960 A1    Aug. 15, 2013

Related U.S. Application Data

(60) Provisional application No. 61/367,591, filed on Jul. 26, 2010.

(51) Int. Cl.
| | |
|---|---|
| *C08L 33/12* | (2006.01) |
| *A61L 24/02* | (2006.01) |
| *A61K 47/32* | (2006.01) |
| *A61L 24/04* | (2006.01) |
| *A61K 9/14* | (2006.01) |
| *A61L 24/00* | (2006.01) |
| *A61L 24/06* | (2006.01) |

(52) U.S. Cl.
CPC ............. *A61K 47/32* (2013.01); *A61L 24/0015* (2013.01); *A61L 24/02* (2013.01); *A61L 24/043* (2013.01); *A61L 24/06* (2013.01); *A61L 2300/252* (2013.01); *A61L 2300/402* (2013.01); *A61L 2300/406* (2013.01); *A61L 2300/414* (2013.01); *A61L 2300/416* (2013.01); *A61L 2300/44* (2013.01); *A61L 2300/442* (2013.01)

(58) Field of Classification Search
None
See application file for complete search history.

(56) References Cited

U.S. PATENT DOCUMENTS

| | | | |
|---|---|---|---|
| 2004/0132859 A1* | 7/2004 | Puckett, Jr. et al. | 523/118 |
| 2004/0226479 A1 | 11/2004 | Lyles et al. | |
| 2005/0256220 A1 | 11/2005 | Lavergne et al. | |
| 2007/0027230 A1 | 2/2007 | Beyar et al. | |
| 2007/0048382 A1* | 3/2007 | Meyer et al. | 424/487 |
| 2009/0264554 A1* | 10/2009 | Meyer et al. | 523/116 |
| 2009/0270527 A1* | 10/2009 | Lin et al. | 523/116 |

FOREIGN PATENT DOCUMENTS

WO    0149327 A2    7/2001

OTHER PUBLICATIONS

International Search Report for PCT/US2011/045338 the counterpart application mailed on Mar. 20, 2012.

* cited by examiner

*Primary Examiner* — James J Seidleck
*Assistant Examiner* — Peter A Salamon
(74) *Attorney, Agent, or Firm* — Sorell Lenna & Schmidt LLP

(57) ABSTRACT

The present invention relates to a composition comprising: a) a first component comprising a poly(methyl met 5 hacrylate) (PMMA), a contrast agent, a radical donor and calcium based particles; and b) a second component comprising methyl methacrylate (MMA), a radical scavenger, and a polymerization accelerator; wherein the composition has an average setting time of about 13 minutes.

11 Claims, No Drawings

CALCIUM PARTICLE-EMBEDDED, SNAP-TO-DOUGH, HIGH-VISCOSITY BONE CEMENT

BACKGROUND

The present invention relates generally to a bone cement composition, a kit and a method of making the bone cement composition.

Any publications or references discussed herein are presented to describe the background of the invention and to provide additional detail regarding its practice. Nothing herein is to be construed as an admission that the inventors are not entitled to antedate such disclosure by virtue of prior invention.

Bone cement compositions are useful in applications such as dental and medical procedures. In particular, they are frequently used in bonding or affixing an implant material to natural bone and to repair damaged natural bone.

Typically, current bone cement compositions are sold in two-part preparations containing a powder (or dry) part and a liquid (or wet) part, which, when combined, polymerize to form a hardened substance mimicking many of the physical properties of natural bone. The powder part typically includes a polymeric material, such as acrylate polymers, while the liquid part includes a reactive monomer, such as methylmethacrylate. Recent developments have focused on modifying the bone cement composition for particular medical procedures.

For example, to attach prostheses to bone, Faccioli et al. (U.S. Pat. No. 5,004,501) discloses a bone cement composition having a polymer with submicron particle size, i.e. less than 0.9 microns. As stated in Faccioli et al., the function of the submicron particles is to fill any voids left in the bone cement composition to produce stronger bone cement. The patent further discloses the use of fluoride salts to produce a stronger bond between the bone cement and the bone of the patient.

For particular medical applications such as vertebroplasty, manufacturers have turned to producing bone cement compositions having radiopacity and longer setting times. For example, Lavergne et al. (U.S. Patent Application No. 2005/0256220) describes a polymethyl methacrylate (PMMA)-based bone cement having setting times greater than 15 minutes and a high concentration of a radio-opaque component, and optionally calcium phosphate.

In another example of bone cements for vertebroplasty procedures, Voellmicke et al. (U.S. Pat. No. 7,008,433 and U.S. Patent Application No. 2003/0032964) describe a PMMA-based composition to provide radiopacity and further increase the setting time of the bone cement. Specifically, the bone cement composition has a setting time that is at least greater than 18 minutes. To produce a bone cement with a higher setting time and increased radiopacity, Voellmicke et al. use barium sulfate at amounts of 20% by weight to 40% by weight. The barium sulfate particles have D50 sizes of greater than 3 microns and require 50% of the barium sulfate particles to be unbound (i.e. free) from the PMMA particles.

Other applications have focused on increasing the viscosity of the bone cement composition at an accelerated rate to infiltrate the medical site and prevent any migration of the cement during medical procedures. In particular, Beyar et al. (U.S. Patent Application Nos. 2007/0027230 and 2007/0032567), focus on a viscosity greater than 500 Pascal-second at 2 minutes after the initiation of mixing the two components of the bone cement composition. The U.S. Patent Applications of Beyar et al. claim to achieve a high viscosity at an expedited rate by using one or more sub-population of PMMA beads with a molecular weight that is significantly different than a main population of PMMA beads. In general, the PMMA beads are incorporated into a cement by polymer growth and attachment initiated through the double bond of a monomer and/or on the surface of the PMMA beads and the presence of an initiator.

Other U.S. patents and publications describing various tools, cements and methods for treating bone include, U.S. Pat. No. 4,494,535, U.S. Pat. No. 4,653,487, U.S. Pat. No. 4,653,489, U.S. Pat. No. 4,969,888, U.S. Pat. No. 5,108,404, U.S. Pat. No. 5,276,070, U.S. Pat. No. 5,336,699, U.S. Pat. No. 6,383,188, U.S. Pat. No. 6,383,190, U.S. Pat. No. 6,348,055, and U.S. Patent Publications 2003/0109883; 2002/0068974; 2004/0260303; and 2007/0087031.

While there have been attempts to reduce cement leakage by injecting more viscous cement, for example, during the doughing time, the hardening time of PMMA cements is still considered to be too long. In addition, typical PMMA formulations result in a failure strength material that has been reported to over compensate the augmented vertebra which then in turn increases the probability of failure in adjacent vertebrae. Hence, it would be desirable to provide a fast setting bone cement with a lower failure strength, and or improved osteoconduction.

SUMMARY OF THE INVENTION

The present invention provides a rapid dough time, for example, a powdered polymer and liquid monomer may be mixed to form a toothpaste-like, "doughy" consistency suitable for injection. In an exemplary embodiment, the invention provides a rapid dough time PMMA based cement having a lower stiffness, for example, between about 50 MPa and about 930 MPa, that reduces the risk of fracture in adjacent vertebral bodies, improves integration of neighboring bone, and provides the clinician with a product having better handling properties. In another embodiment, the invention provides a settable bone cement wherein the stiffness is lowered by the inclusion of additives such as PEG-acrylates, urethanes and others in combination with a plurality of calcium based particles in the cement, for example, the calcium in the particles may be in the form of hydroxyapatite (HA), tricalcium phosphate (TCP), mixtures of HA-TCP, calcium phosphate, calcium sulfate, and/or calcium carbonate. In another exemplary embodiment, the invention provides a method comprising mixing a plurality of calcium based particles with a bone filling material to form an improved bone augmentation material. The plurality of calcium based particles may induce bone growth into and around the cement and/or inhibit the formation of an intervening fibrous tissue layer on the surface of the hardened PMMA cement.

In yet another exemplary embodiment, the invention provides a PMMA bone cement that is useful in the augmentation of a vertebral body during kyphoplasty or vertebroplasty for the treatment of vertebral compression fractures.

In another exemplary embodiment, the invention provides a bone cement having a first stage in which the cement obtains a highly viscous dough like consistency within a period of time less than about 4 minutes, less than about 3 minutes, less than about 2 minutes, less than about 1 minutes, or less than about 30 seconds, and wherein the dough like consistency is maintained for at least 5 minutes and the plurality of calcium particles are movable within the cement, and a second stage where the plurality of calcium based particles are suspended and immovable within the cement.

DETAILED DESCRIPTION OF THE INVENTION

For the purposes of promoting an understanding of the principles of the invention, reference will now be made to certain embodiments and specific language will be used to describe the same. It will nevertheless be understood that no limitation of the scope of the invention is thereby intended, such alterations and further modifications in the illustrated device, and such further applications of the principles of the invention as described herein being contemplated as would normally occur to one skilled in the art to which the invention relates.

The uses of the terms "a" and "an" and "the" and similar references in the context of describing the invention (especially in the context of the following claims) are to be construed to cover both the singular and the plural, unless otherwise indicated herein or clearly contradicted by context.

Recitation of ranges of values herein are merely intended to serve as a shorthand method of referring individually to each separate value falling within the range, unless otherwise indicated herein, and each separate value is incorporated into the specification as if it were individually recited herein.

All methods described herein may be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

As used herein, "comprising," "including," "containing," "characterized by," and grammatical equivalents thereof are inclusive or open-ended terms that do not exclude additional, unrecited elements or method steps, but will also be understood to include the more restrictive terms "consisting of" and "consisting essentially of."

As used herein, "substantially free" means the object or composition is present in an amount less than 0.01% by weight of the total composition.

As used herein, "cure" means the cement has hardened to a viscosity of at least 2000 Pa-s.

As used herein, a "PMMA based cement" or a "bone cement" means a Polymethylmethacrylate (PMMA) based composition typically formulated as a two-part preparation having a dry part and a liquid part, which, when combined, polymerize to form a hardened substance, wherein the dry part includes a polymeric material, such as acrylate polymers, such as PMMA polymers, and may optionally include a contrast agent and/or a radical donor, while the liquid part includes a reactive monomer, such as methylmethacrylate, and may optionally include a radical scavenger and/or a polymerization accelerator.

The stress-strain curves for the compositions of the invention may be measured using circular specimens (for example, 5-6 mm in diameter by 2-3 mm thick) with a dynamic mechanical analyzer (such as the Perkin-Elmer, DMA-7), in a parallel plate configuration, at a creep rate of 2.9 kPa/min. The compressive modulus can be determined as the slope of the best linear fit of the stress-strain curves in the linear region.

In a particular embodiment, a bone cement composition includes a first component and a second component. The first component includes a pre-polymerized vinyl polymer, a contrast agent, calcium particles (e.g., hydroxyapatite particles or TCP particles) and a radical donor. The second component includes a reactive monomer, a radical scavenger, and a polymerization accelerator. The composition is a bone cement that has an average setting time of about 13 minutes. The bone cement composition is typically prepared by homogeneously mixing the first component with the second component using any suitable mixing method.

The first component of the bone cement composition is referred to as a dry or powder component. In an exemplary embodiment, the first component includes a pre-polymerized vinyl polymer. Pre-polymerized vinyl polymers include, for example, any medically suitable pre-polymerized polymers containing vinyl groups. Exemplary medically suitable pre-polymers include pre-polymerized acrylate polymers such as poly(methyl methacrylate) (PMMA), pre-polymerized styrene acrylates, poly-methacrylate, poly-ethacrylate, poly-butylmethacrylate, copolymers, and mixtures thereof. In an exemplary embodiment, the pre-polymerized vinyl polymer is poly(methyl methacrylate) (PMMA).

Typically, the pre-polymerized vinyl polymer has a molecular weight of about 200,000 grams/mole to about 500,000 grams/mole. In an embodiment, the pre-polymerized vinyl polymer has an average particle size up to about 100.0 microns. In an embodiment, the pre-polymerized vinyl polymer has an average particle size of about 1.0 micron to about 100.0 microns. In a particular embodiment, the pre-polymerized vinyl polymer has an average particle size of about 35 microns to about 60 microns. In an embodiment, greater than 99.0% of the particles of the pre-polymerized vinyl polymer have a particle size of greater than about 1.0 micron.

The pre-polymerized polymer is typically present in the bone cement composition at about 5.0% by weight to about 40.0% by weight of total weight of the first component. In a particular embodiment, the pre-polymerized polymer is present in the bone cement composition at about 10% by weight to about 30% by weight, such as about 12% to about 30% by weight, about 12% by weight to about 24% by weight, or about 15% by weight to about 30% by weight. of the total weight of the first component.

The first component of the bone cement composition further includes a radical donor. The radical donor is typically used to initiate a polymerization reaction with the reactive monomer present in the second component. In an embodiment, any known radical donor may be used. In an exemplary embodiment, the radical donor may be benzoyl peroxide (BPO), azo-bis-isobutyrylnitrile (AIBN), and mixtures thereof. In a particular embodiment, the radical donor is benzoyl peroxide (BPO). Typically, the radical donor is present at not greater than about 3.0% by weight of the total weight of the first component. In an exemplary embodiment, the radical donor is present at about 0.5% by weight to about 3.0% by weight, such as about 0.8% by weight to about 3.0% by weight, such as about 0.8% by weight to about 2.0% by weight, such as about 1.5% by weight to about 2.0% by weight of the total weight of the first component.

The first component of the bone cement composition may optionally further includes a contrast agent. The contrast agent may be selected depending on the medical instrumentation used to view the contrast agent. Suitable contrast agents include, for example, barium sulfate ($BaSO_4$), zirconium dioxide, $CHI_3$, $Na_2FPO_3$, and $CaF_2$. In an exemplary embodiment, the contrast agent is barium sulfate. Typically, the barium sulfate contrast agent may be imaged by fluoroscopy. In an embodiment, the barium sulfate is present at an amount sufficient to allow continuous imaging by fluoroscopy during the medical procedure, such as the injection of the bone cement in a patient, without impacting the mechanical properties or the desired setting time of the bone cement. The contrast agent is typically present at not less than about 5% by weight of the total weight of the first component. In an embodiment, the contrast agent is present at about 2% by weight to about 35% by weight, such as about 5% by weight to about 20% by weight, such as about 8% by weight to about 12% by weight, or about 10% by weight of the total weight of the first component.

The first component of the bone cement composition further includes a plurality of calcium based particles, for example, hydroxyapatite (HA), tricalcium phosphate (TCP), mixtures of HA-TCP, calcium phosphate, calcium sulfate, and/or calcium carbonate particles. In an exemplary embodiment, the calcium particle has an average particle size of about 5 microns to about 350 microns, such as about 5 microns to about 100 microns.

The first component can further include optional ingredients. Optional ingredients include, for example, antibiotics, cytostatis agents, analgesic agents, disinfectants, preservatives, growth factors, proliferative factors, proteins, peptides, biopolymers, dyes, and mixtures thereof. In an exemplary embodiment, the optional ingredient includes gentamycine, tobramycine, clindamycine, vancomycine, $\beta$-TGF or an analog thereof, a bone morphogenic protein series compound, and mixtures thereof. Additionally, the bone cement composition is substantially free of fluoride salt.

The second component of the bone cement composition is generally referred to as a liquid component. The second component includes a reactive monomer, which reacts with the radical donor and polymerizes. In an embodiment, the reactive monomer is a methyl methacrylate (MMA), PEG monoacrylates, PEG diacrylates, PEG monomethylacrylates, PEG dimethyacrylates, PEG-mono/di-acrylates/methyacrylate, butanediol methacrylates, polyolefin-acrylates, urethaneacrylates, methacrylates, and mixtures thereof. Among the PEG-based reactive monomers, they typically have a molecular weight of about 200 Daltons (D) to about 1500 D. In an exemplary embodiment, the reactive monomer is methyl methacrylate (MMA).

The second component typically includes about 10.0% by weight to about 99.9% by weight of the reactive monomer, based on the total weight of the second component. In another exemplary embodiment, the reactive monomer is present at about 80% by weight to about 99.9% by weight, such as about 95.0% by weight to about 99.9% by weight, such as about 98.5% by weight to about 99.9% by weight of the total weight of the second component.

In yet another exemplary embodiment, the second component includes a polymerization accelerator. Typically, the polymerization accelerator is selected such that the polymerization reaction occurs at or below normal body temperatures so as not to cause thermal damage to the surgical site or surrounding areas. In an embodiment, the polymerization accelerator is a tertiary amine. In an exemplary embodiment, the tertiary amine includes, but is not limited to, dimethylparatoluidine (DMPT) and/or dihydroxyethylorthotoluidine. For instance, the polymerization accelerator is present at less than about 1.0% by weight, such as even less than about 0.5% by weight of the total weight of the second component. In an embodiment, the polymerization accelerator is present at about 0.2% by weight to about 1.0% by weight, such as about 0.2% by weight to about 0.5% by weight of the total weight of the second component.

In another exemplary embodiment, the second component further includes a radical scavenger. Typically, the radical scavenger is present to retard or arrest the ability of the reactive monomer to self-polymerize. Exemplary radical scavengers include, but are not limited to, hydroquinone, hydroquinone monomethylether, vitamin E, and mixtures thereof. In an exemplary embodiment, the radical scavenger is hydroquinone monomethylether.

The second component may further include ingredients such as a diluent, a dye, an admixture of proteins, a chemotherapeutic, a drug, an antibiotic, and mixtures thereof. The admixture of proteins may include, for example, an admixture of heat sensitive/unsensitive proteins such as mitogenic growth factors, morphogenic growth factors, and mixtures thereof. An example of a suitable drug that can be included in the second component is bisphophonate.

In an exemplary embodiment, the weight ratio of the first component to the second component is about 2.2:1 to about 3.3:1, such as about 2.5:1. Further, the mixing may be done by any suitable mixing device.

Once mixing of the first component and the second component is initiated, the viscosity of the bone cement composition reaches a viscosity of at least 200 Pascal-second (Pa-s) at a time of less than about 4 minutes, less than about 3 minutes, less than about 2 minutes, less than about 1 minute, or less than about 30 seconds. In an exemplary embodiment, the viscosity of the bone cement reaches a viscosity of about 1000 Pa-s at a time of greater than about 5:30 minutes, greater than about 6:00 minutes, greater than about 7:00 minutes, greater than about 8:00 minutes, or greater than about 9:00 minutes.

In an exemplary embodiment, the bone cement composition advantageously exhibits desirable properties when cured. For instance, the bone cement composition has a compression strength when cured that is closer to the compression strength of natural bone, reduces the risk of fractures in adjacent vertebral bodies, improves bone growth into and around the cement, reduces the growth of an intervening fibrous tissue layer around or in contact with the cement, and combinations thereof. In an exemplary embodiment, the compression strength of the bone cement composition may be tested after 6 days on a Zwick testing machine Z010, according to ASTM F451-99a and ISO 5833 standards and it is less than about 930 MPa, less than about 500 MPa, less than about 400.0 MPa, less than about 300.0 MPa, less than about 200.0 MPa, less than about 100.0 MPa.

In an exemplary embodiment, the components of the composition are capable of being readily injectable through a syringe-like device or other delivery mechanism to a surgical site, where they react to form the composition and cure to the hardened state. The composition is persistent at the surgical site, with the calcium particles providing a means for the cement to adhere to the neighboring bone. It is to be appreciated, however, that in exemplary embodiments of the compositions, while satisfying at least some of these advantages, the composition may not satisfy all of these advantages in every instance.

In an embodiment, the composition is sold and distributed to users in a kit where the first and second components are maintained apart (e.g., separately packaged or contained) until they are ready for use in forming the composition. The user may receive a mixer apparatus containing the components in separate compartments thereof. See generally, U.S. Pat. No. 6,241,734, U.S. Pat. No. 6,613,054, U.S. Pat. No. 7,018,089, and U.S. Patent application publication No. 2002/0191487 A1. These publications generally describe suitable apparatus for mixing and delivering the composition's components and mixtures thereof. The components likely will be mixed by the user immediately prior to the surgical procedure with a suitable mixing apparatus and will form a dough-like consistency within a very short time after mixing.

The composition may be applied using a variety of mechanisms such as, for example, those described in U.S. Pat. Nos. 5,972,015 and 6,066,154. These patents generally describe a procedure referred to as "Kyphoplasty", which uses one or two balloons, similar to angioplasty balloons, to reduce the vertebrae bone fracture and restore vertebral height prior to injecting a bone cement composition. In an example, two balloons are introduced into the vertebra via bilateral transpedicular cannulae. The balloons are inflated to reduce the fracture, then deflated and removed, leaving a relatively empty cavity into which a bone cement composition is injected. The inflation of the balloons and subsequent injection of the composition helps restore vertebral height.

The invention will now be more particularly described with reference to the following specific examples. It will be understood that these examples are illustrative and not limiting of the embodiments of the invention.

EXAMPLE 1

Formulations are prepared for a performance study. Specifically, the setting time of the formulations are measured varying amounts of polymerization accelerator. A first component (i.e. a dry or powder component) is prepared by combining 100.0 g of prepolymerized methylmethacrylate (PMMA) (Plex 6612, Röhm GmbH, Germany) and 50.0 g PMMA (Plex 332, Röhm GmbH, Germany) and 1.62 g Benzoylperoxide (50% attenuated) plus 150.0 g sintered Hydroxyapatite.

A liquid component is prepared using 30% Butyl-di-methacrylate (BDMA), 70% Methylmethacrylate (MMA), 100 ppm Hydrquinone-monomethyl-ether and 0.5% Di-methyl-para-toluidine.

The liquid to powder ratio is 8 grams of liquid to 20 grams of powder, with the mixing of the liquid and powder for 15 seconds resulting in a highly doughy paste with a chewing gum like consistency.

Start of mixing=0 seconds

Mixing time=15 seconds

Dough state (start of working time) is about 45 seconds and the end of working time is about 11 minutes.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected. In addition, all publications cited herein are hereby incorporated by reference in their entirety.

What is claimed is:

1. A composition comprising:
   a) a first component comprising a poly(methyl methacrylate) (PMMA), a contrast agent, a radical donor and calcium based particles, the PMMA having a molecular weight of about 200,000 grams/mole to about 500,000 grams/mole, the calcium based particles comprising hydroxyapatite particles having an average particle size of about 5 microns to about 100 microns; and
   b) a second component comprising methyl methacrylate (MMA), a radical scavenger, and a polymerization accelerator;
      wherein the composition has an average setting time of about 13 minutes and a stiffness of between about 50 MPa and about 930 MPa.

2. The composition of claim 1, wherein the calcium based particles further include calcium based compositions selected from the group consisting of tricalcium phosphate (TCP), mixtures of hydroxyapatite (HA) and TCP, calcium phosphate, calcium sulfate, calcium carbonate and mixtures thereof, tricalcium phosphate (TCP), mixtures of HA-TCP, calcium phosphate, calcium sulfate, calcium carbonate and mixtures thereof.

3. The composition of claim 1 wherein the calcium based particles are present at not less than about 10% by weight of the total weight of the first component.

4. The composition of claim 1, wherein the calcium based particles are present at about 40% by weight to about 75% by weight of the total weight of the first component.

5. The composition of claim 1, wherein the contrast agent is selected from the group consisting of barium sulfate (BaS04), zirconium dioxide, CHI3, Na2FP03, and CaF2, and mixtures thereof.

6. The composition of claim 5, wherein the contrast agent has an average particle size of about 0.3 microns to about 10 microns.

7. The composition of claim 1, wherein the radical donor is selected from the group consisting of benzoyl peroxide (BPO), azo-bis-isobutyrylnitrile (AIBN), and mixtures thereof.

8. The composition of claim 7, wherein the radical donor is present at about 1.5% by weight to about 2.0% by weight of the total weight of the second component.

9. The composition of claim 1, wherein the radical scavenger is selected from the group consisting of hydroquinone monomethylether, hydroquinone, vitamin E, and mixtures thereof.

10. The composition of claim 1, wherein the polymerization accelerator is selected from the group consisting of dimethylparatoluidine (DMPT), dihydroxyethylorthotoluidine, and mixtures thereof.

11. The composition of claim 1, further comprising an optional ingredient selected from the group consisting of an antibiotic, a cytostatic agent, an analgesic agent, a disinfectant, a preservative, a growth factor, a proliferative factor, a protein, a peptide, a biopolymer, a dye, a chemotherapeutic, a drug, and mixtures thereof.

* * * * *

UNITED STATES PATENT AND TRADEMARK OFFICE
CERTIFICATE OF CORRECTION

PATENT NO. : 9,107,951 B2
APPLICATION NO. : 13/812364
DATED : August 18, 2015
INVENTOR(S) : Lee et al.

It is certified that error appears in the above-identified patent and that said Letters Patent is hereby corrected as shown below:

Title Page

Item (75), under "Inventors", in Column 1, Line 3, delete "Wollstadt" and insert -- Wöllstadt --, therefor.

Item (75), under "Inventors", in Column 1, Line 4, delete "A" and insert -- A. --, therefor.

Item (73), under "Assignee", in Column 1, Line 1, delete "SARL, Neuchatel" and insert -- SÀRL, Neuchâtel --, therefor.

Item (57), under "ABSTRACT", in Column 2, Line 2, delete "poly(methyl met 5 hacrylate)" and insert -- poly(methyl methacrylate) --, therefor.

Specification

In Column 4, Line 39, delete "weight." and insert -- weight --, therefor.

In Column 4, Line 47, delete "azo-bis-isobutyrylnitrile" and insert -- azo-bis-isobutyronitrile --, therefor.

In Column 5, Lines 34-35, delete "dimethyacrylates, PEG-mono/di-acrylates/methyacrylate," and insert -- dimethacrylates, PEG-mono/di-acrylates/methacrylate, --, therefor.

In Column 6, Line 13, delete "bisphophonate." and insert -- bisphosphonate. --, therefor.

In Column 7, Line 34, delete "Hydrquinone-monomethyl-ether" and insert -- Hydroquinone-monomethyl-ether --, therefor.

Signed and Sealed this
Twenty-ninth Day of March, 2016

Michelle K. Lee
*Director of the United States Patent and Trademark Office*

CERTIFICATE OF CORRECTION (continued)

Claims

In Column 8, Line 28, in Claim 5, delete "(BaS04), zirconium dioxide, CHI3, Na2FP03, and CaF2," and insert -- ($BaSO_4$), zirconium dioxide, $CHI_3$, $Na_2FPO_3$, and $CaF_2$, --, therefor.

In Column 8, Line 36, in Claim 7, delete "azo-bis-isobutyrylnitrile" and insert -- azo-bis-isobutyronitrile --, therefor.